United States Patent [19]

Thomas

[11] 4,109,514
[45] Aug. 29, 1978

[54] RHEOMETER AND USES THEREOF

[75] Inventor: David Hamilton Thomas, Middlesbrough, England

[73] Assignee: Imperial Chemical Industries Limited, London, England

[21] Appl. No.: 767,948

[22] Filed: Feb. 11, 1977

[30] Foreign Application Priority Data

Feb. 17, 1976 [GB] United Kingdom ............... 6183/76
May 19, 1976 [GB] United Kingdom ............. 20676/76

[51] Int. Cl.² .......................................... G01N 11/00
[52] U.S. Cl. ..................................... 73/58; 73/150 R
[58] Field of Search .......................... 73/58, 59, 150

[56] References Cited

U.S. PATENT DOCUMENTS

| 2,101,322 | 12/1937 | Reed | 73/58 |
| 2,762,219 | 9/1956 | Prentiss | 73/58 X |
| 3,869,984 | 3/1975 | Toth | 73/150 X |
| 3,901,069 | 8/1975 | van Gastel | 73/150 X |

Primary Examiner—Richard C. Queisser
Assistant Examiner—Joseph W. Roskos
Attorney, Agent, or Firm—Cushman, Darby & Cushman

[57] ABSTRACT

A rheometer comprises adjacent surfaces moveable relative to one another e.g. a pair of rollers, means e.g. a motor for moving one or both surfaces and means for measuring the effect of or on the movement when a sample under test e.g. a sheet moulding composition is placed between and in contact with the surfaces.

19 Claims, 3 Drawing Figures

RHEOMETER AND USES THEREOF

The present invention relates to a rheometer and to its use in testing the plasticity and viscosity of materials.

The rheometer comprises:
(a) adjacent surfaces movable relative to one another said surfaces being adapted so that they can be placed into contact with opposite sides of material under test,
(b) means for moving, while remaining in contact with the material, one or both surfaces relative to each other and,
(c) means for measuring the effect of the material between and in contact with the adjacent surfaces on the rate of relative movement under a constant applied force, or on the force required to generate a constant rate of relative movement, or on one surface as a result of movement of the other. All of these measurements may be considered as being a measurement of the torque imparted to one of the adjacent surfaces by movement of the other surface when test material is under pressure between the surfaces.

One or both of the adjacent surfaces are preferably rollers. It is usually convenient for one of the surfaces to be stationary, the other being movable. The surfaces should be uniform so as to give a constant frictional resistance and to this end they may be polished, e.g. polished steel, or uniformly roughened. It is also preferred that the adjacent surfaces be adjustable with respect to one another to vary their distance apart so as to accomodate material of varying thicknesses under a constant and predetermined pressure. This may be achieved most conveniently by maintaining one of the surfaces in a fixed position the other surface being adjustable in relation thereto.

The means for moving one or both of the surfaces relative to one another is preferably an electric motor although obvious equivalents such as mechanical or pneumatic motors may also be used.

The instrument measures the effect of the material between and in contact with the adjacent surfaces on the rate of relative movement under a constant applied force, or on the force required to generate a constant rate of relative movement, or on one surface as a result of movement, usually at a constant rate, of the other. The values obtained are in effect a measure of the shear stress of the material under test. In the case of one surface comprising a rotating roller the torque of the shaft driving the roller or its speed of rotation may be measured by known means, suitably electronically, the values obtained being intermittently registered or continuously recorded. Alternatively the rotating roller may be driven at constant speed and the effect on the other surface measured e.g. if the other surface is a roller, the torque imparted to this roller may be measured and recorded.

It is advantageous for one at least of the two surfaces to be capable of being maintained at a constant temperature which can be varied as desired. This may be achieved by electrical means or by use of a liquid heat transfer medium. For example, one of the surfaces may be in the form of a drum which may be filled with a fluid such as a mineral oil held at a constant desired temperature, e.g. 0° to 200° C.

The apparatus according to the invention may be used in a wide range of aplications where the material under investigation has a high viscosity. It finds use therefore in the food industry, in the testing of doughy and rubber or plastic materials and also in the plastics industry particularly in the field of sheet moulding compounds. In most uses the instrument may be used to compared the rheological properties of a sample under test with the same properties of a sample known to be satisfactory in service. In this manner the machine is in fact calibrated against the known sample.

The use of the instrument provides a method of testing which comprises placing the sample under test between and in contact with adjacent surfaces, moving said surfaces while remaining in contact with the material, at different speeds relative to one another, measuring the effect of the sample on the rate of relative movement under a constant applied force, or on the force required to generate a constant rate of relative movement, or on one surface as a result of movement of the other and comparing the measurement with a measurement of a comparable sample known to be satisfactory in practice.

An important use of the apparatus and method is in the field of unsaturated polyester resins which are well known commercial materials which consist of the product of copolymerising an ethylenically unsaturated polyester with an ethylenically unsaturated comonomer so that the polyester is cross-linked to produce a solid resin. For many applications the two components are used in conjunction with a reinforcing material such as chopped glass fibres so that the final polymerised article or structure has greater strength. One form in which such a reinforced composition is used is as a "sheet moulding compound" in which the polyester, comonomer and reinforcing material are in the form of a sheet which can be formed into the desired shape and then polymerised or cured, e.g. by the application of heat.

The unsaturated polyester and comonomer are, usually, liquid and in order to prevent them draining out of the reinforcing material it is customary to add a thickening agent, commonly magnesium oxide, which by chemical reaction causes the polyester/comonomer solution to thicken so that it does not flow from the reinforcing material but does allow it to flow in the mould. The thickening process generally takes a period of time to complete so that the sheet moulding compound is not immediately ready for moulding. The present invention provides a method of testing a sheet moulding compound to decide whether it is suitable for use. The method may also be used to test the suitability of other plastic moulding compounds either thermoplastics e.g. PVC, or uncured thermosettable compositions.

It is one of the advantages of the present method that it can be used to test sheet moulding compounds which are being manufactured continuously. Thus the sheet may pass continuously between the adjacent surfaces e.g. rollers and by means of a suitable recorder the condition of the sheet along its length may be determined by intermittently moving the surfaces into contact with the sheet and taking a measurement. It is also an advantage of the method that the polyethylene sheet which usually covers the surfaces of an unsaturated polyester sheet moulding compound need not be removed for the test to be carried out. In this case it is preferred that the surfaces be roughened.

IN THE DRAWINGS

Figure 1:
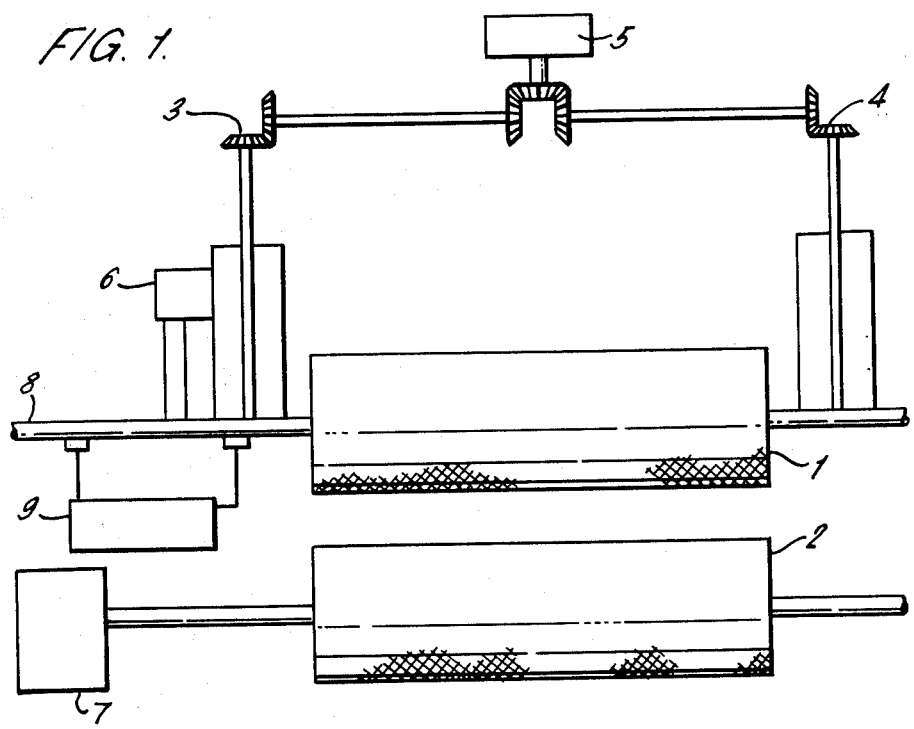
FIG. 1 is an elevational view of a rheometer embodying the principles of the present invention.

FIG. 1 shows one form of the apparatus which comprises two mild steel rollers 1 and 2 with diamond knurled surfaces. Roller 1 mounted on shaft 8 is stationary and does not rotate but is movable up and down by means of screws 3 and 4 controlled by a knurled nut 5 so that a known pressure as indicated by gauge 6 can be exerted on sheet moulding compound between the rollers. The second roller 2 is fixed in position but is rotatable at constant speed by means of motor 7 the time for which it rotates being preset and the rotation automatically stopped when this time is reached. The torque exerted on the shaft 8 is measured electrically and recorded by recorder 9, the instrument being precalibrated so that torque is converted to kilopascals.

Figure 2:
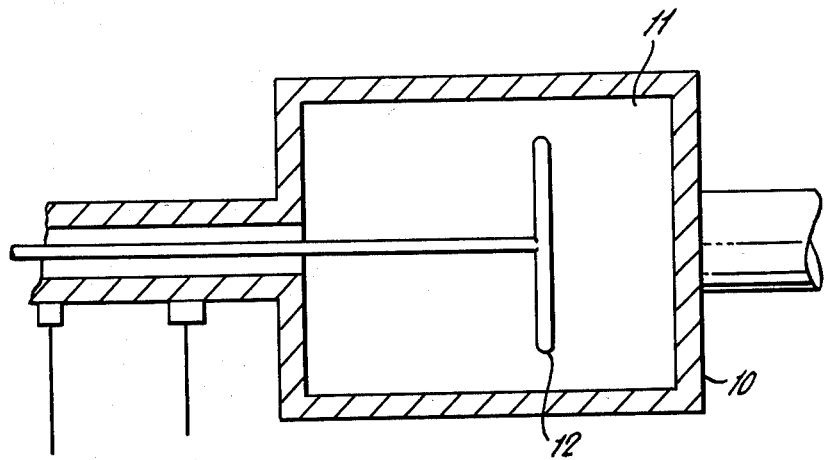
FIG. 2 is a sectional view of a modified form of roller.

FIG. 2 shows a preferred modification of roller 2 which now consists of a hollow cylinder 10 containing oil 11 and a heating element 12. The cylinder is rotatable and the presence of the element and the oil enables the cylinder surface to be maintained at a constant temperature.

Figure 3:
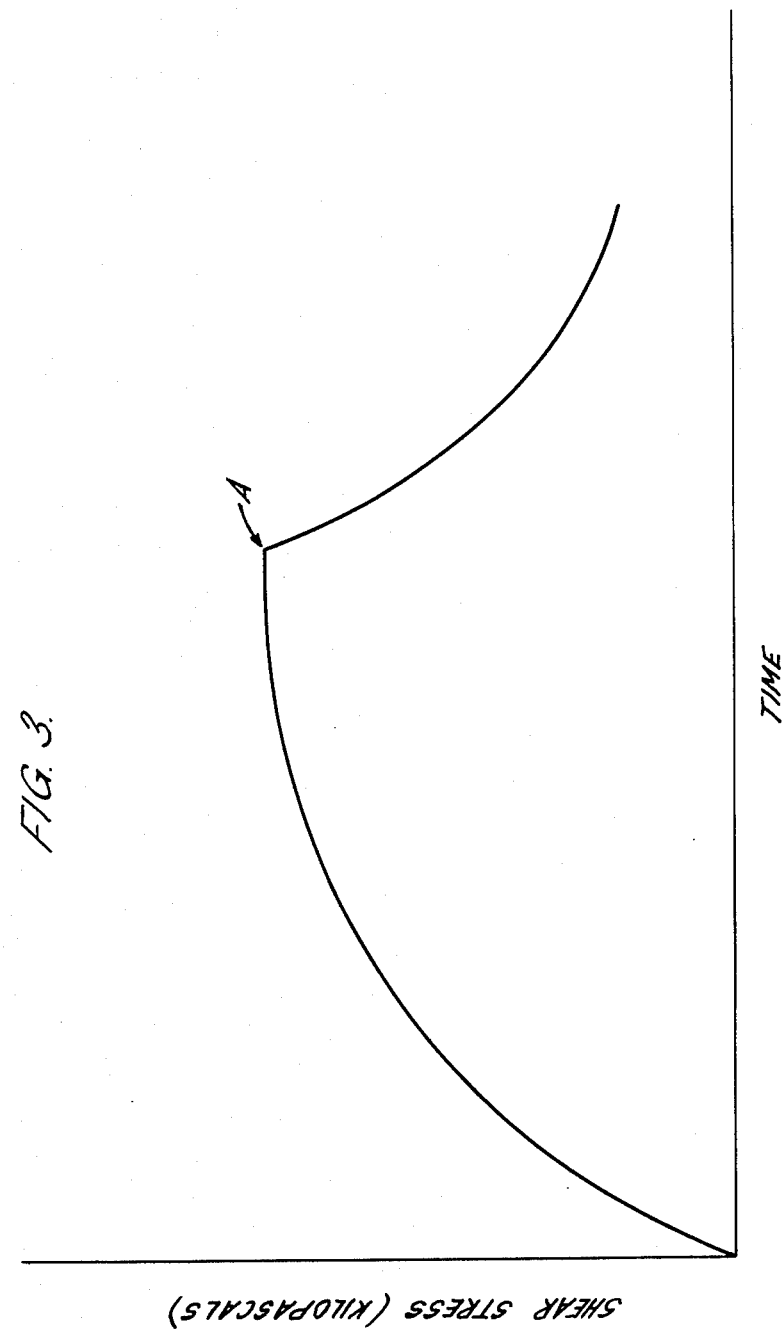
FIG. 3 is a graph of shear stress versus time.

In operation a sample e.g. of sheet moulding composition, comprising an unsaturated polyester resin and glass fibre, is placed between the rollers and held in position by tightening nut 5. Roller 2 as shown in FIG. 2 containing oil at a temperature of 20° C is caused to rotate for a period of 2 minutes when a recorded trace as shown in FIG. 3 is obtained the trace being a plot of shear stress in kilopascals against time, point A being the time at which the roller 2 was stopped. The trace is indicative of the flowability of the sample under test the height of the curve being a measure of its stiffness. Different samples give different curve shapes and heights but for a given composition its suitability for use in moulding can be decided by comparison of its trace with the trace of a sample made from the same materials and which has proved suitable in practice.

I claim:

1. A rheometer which comprises:
   (a) two rollers disposed in spaced-apart relationship with their axes parallel and located so that they can be placed into contact with opposite sides of a material under test said rollers being rotatable relative to one another while remaining in contact with said material, and means for adjusting the distance between said rollers so that test material of varying thicknesses can be accommodated in the space between them in contact with both rollers under constant and predetermined pressure,
   (b) means for rotating one of said rollers and,
   (c) means for maintaining the material under test under constant pressures by the surfaces and,
   (d) a torque measuring device connected to one of said rollers for measuring the torque imparted to the latter upon rotation of and said roller when test material is under pressure between said rollers.

2. A rheometer according to claim 1 in which one at least of the rollers is capable of being maintained at a constant temperature which can be varied as desired.

3. A rheometer according to claim 2 in which the roller is heated by means of a liquid heat transfer medium.

4. A rheometer according to claim 3 in which one of the rollers is in the form of a drum which is filled with a fluid which can be held at a constant desired temperature.

5. A rheometer according to claim 1 in which the means for rotating said roller is an electric motor.

6. A rheometer according to claim 1 wherein one roller is a stationary roller having a uniformly roughened surface and the other roller is a rotatable drum having a uniformly roughened surface and filled with a liquid which can be maintained at a constant desired temperature, and wherein said rotating means includes a motor for rotating said drum at constant speed, the torque measuring device being connected to the stationary roller so that the torque imparted to the roller through the test material by the rotating drum may be measured thereby obtaining values which are a measure of the shear stress in the material under test.

7. A rheometer according to claim 6 including means for recording said values continuously as units of stress over a period of time.

8. A rheometer according to claim 1 including means for converting the torque by means of precalibration to units of stress and for recording the units continuously over a period of time.

9. A rheometer comprising: a non-rotatable roller and a rotatable roller disposed in spaced apart relationship with their axes parallel; means for adjusting one of the rollers toward and away from the other roller so that test material of varying thicknesses can be accommodated in the space between the rollers and in contact with the rollers under constant and predetermined pressure; means for rotating said rotatable roller; and a torque-measuring device connected to one of said rollers for measuring the torque imparted to that roller upon rotation of the rotatable roller and when test material is under pressure between said rollers.

10. A rheometer as in claim 9 wherein said rotatable roller is a hollow drum filled with liquid, and means for maintaining the liquid at a constant predetermined temperature.

11. A rheometer as in claim 9 wherein said means for rotating one of the rollers rotates that roller at constant speed and wherein said torque measuring device is connected to said non-rotatable roller for measuring the torque imparted to said non-rotatable roller through the test material upon rotation of said rotatable roller.

12. A rheometer as in claim 9 wherein said torque measuring device is connected to said rotatable roller for measuring the torque applied to said rotatable roller by said rotating means.

13. A method of testing the rheological properties of a material which comprises placing a sample of the material between and in contact with adjacent surfaces under constant pressure, moving at least one of said surfaces, while remaining in contact with the sample, at a different speed relative to the other surface, measuring the torque imparted to one of said surfaces by movement of the other surface when test material is under pressure between said surfaces, said measurement being a measure of the shear stress in the material under test, and comparing the measurement thus obtained with values from a comparable sample known to be satisfactory in practice.

14. A method as in claim 13 wherein the sample is an unsaturated polyester resin sheet molding compound.

15. A method as in claim 14 wherein said sheets are being manufactured continuously.

* * * * *